Nov. 12, 1963 E. S. BOERNER Plant Pat. 2,300
ROSE PLANT
Filed Oct. 4, 1962
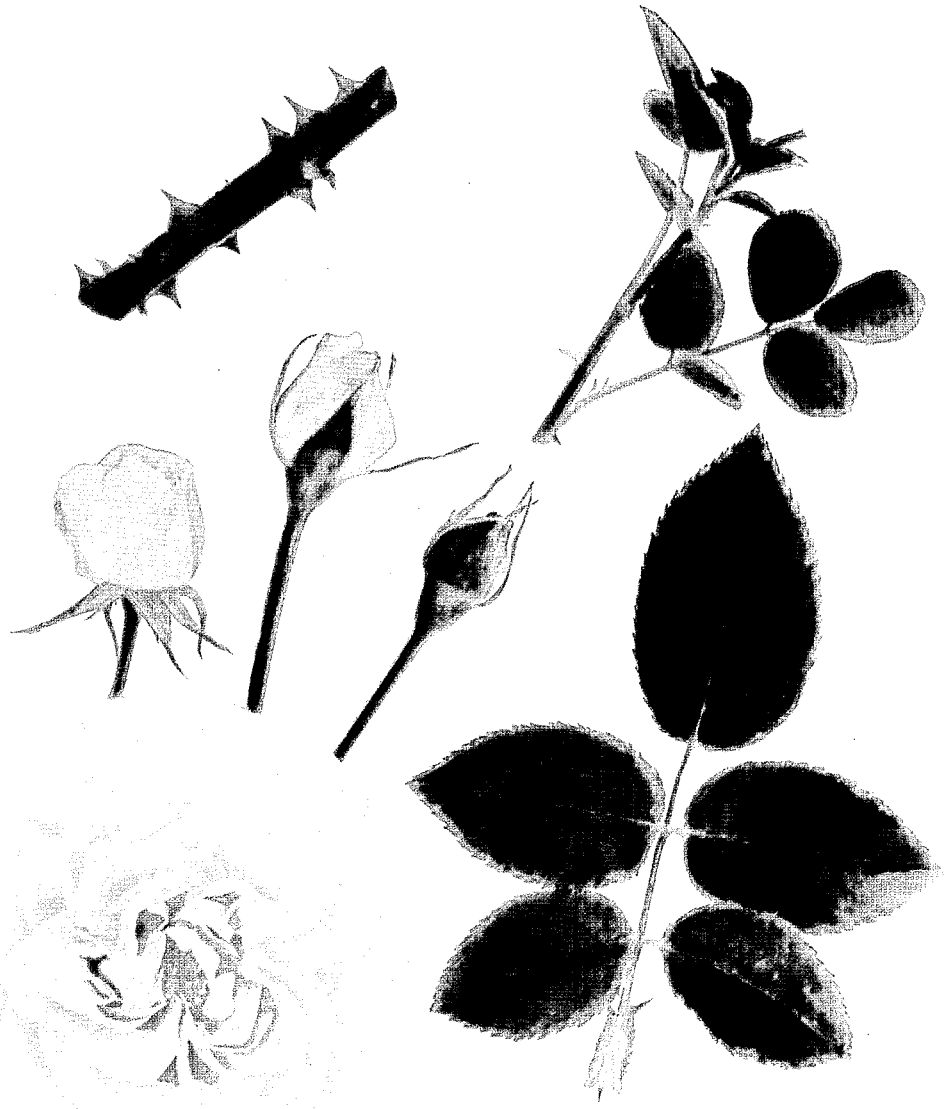
Inventor.
E. S. Boerner
By: Robb & Robb
Attorneys.

United States Patent Office

Plant Pat. 2,300

Patented Nov. 12, 1963

2,300

ROSE PLANT

Eugene S. Boerner, Newark, N.Y., assignor to Jackson & Perkins Company, Newark, N.Y., a corporation of New York

Filed Oct. 4, 1962, Ser. No. 228,509

1 Claim. (Cl. Plt.—11)

The present invention relates to a new and distinct variety of rose plant of the hybrid tea class, which was originated by me by crossing the variety known as "Grey Pearl" (Plant Patent No. 680) with the variety known as "Brownie" (Plant Patent No. 1,720).

The primary objective of this breeding was to produce a new rose variety which bears flowers comparable to those of the parent variety "Grey Pearl," but having the flower color tones accentuated. This objective was fully achieved, along with other desirable improvements, as evidenced by the following unique combination of characteristics which are outstanding in the new variety and which distinguish it from its parents, as well as from all other varieties of which I am aware:

(1) Flower stamens of Deep Chrome color;

(2) A distinctive, attractive and unusual general color tonality of the flowers corresponding to Ochraceous-Salmon, lightly overcast with Carrot Red, said color being rather exotic and far different from any rose color heretofore available; and (3) A fruity flower fragrance.

Asexual reproduction of my new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.

*Seed parent.*—"Grey Pearl."

*Pollen parent.*—"Brownie."

Classification:

*Botanic.*—Hybrid tea.

*Commercial.*—Hybrid tea.

*Flower*

(Observations made from specimens grown outdoors at Newark, New York, in the early morning during the early part of the month of July.)

Blooming habit: Recurrent—continuous.

Bud:

*Size.*—Medium.

*Form.*—Ovoid; is not affected by wet or hot weather.

*Color.*—When sepals first divide—Amaranth Purple, Plate 12. When petals begin to unfurl—Peach Red, Plate 1, with upper half of petals overcast with Eugenia Red, Plate 13. When half-blown: inside of petals—Eugenia Red, Plate 13, lightly overcast with Spinel Red, Plate 26; reverse of petals—Rose Doree, Plate 1, overcast with Light Orange Yellow, Plate 3 in the lower half of the petals.

*Sepals.*—Slightly branched; curl back when petals begin to unfurl. Color: inside—Olivine, Plate 32; outside—Biscay Green, Plate 17, lightly overcast with Carmine, Plate 1 on the outer edges of the sepals.

*Calyx.*—Color—Biscay Green, Plate 17. Shape—funnel. Size—long. Aspect—smooth. Odor when rubbed—none

*Peduncle.*—Length — medium. Aspect — smooth. Strength—erect; slender. Color—Light Bice Green, Plate 17, very lightly overcast with Pompeian Red, Plate 13.

*Opening.*—Opens up well; is not affected by adverse weather conditions.

Bloom:

*Size.*—Large. Average size when fully expanded—from 4½ inches to 5 inches.

*Borne.*—Both singly and several together.

*Stems.*—Medium length; strong.

*Form (when first open).*—Cupped. Permanence—retains its form to the end, but outer petals curl back.

*Petalage.*—Double (full but open center). Number of petals under normal conditions—from 35 to 40.

*Color.*—Center of flower—Apricot Orange, Plate 14, lightly overcast with Rufous, Plate 14. Outer petals—Ochraceous-Salmon, Plate 15, with outer edge of petals very lightly overcast with Rose Doree, Plate 1. Base of petals (aiglet)—Apricot-Yellow, Plate 4. Inside of petals—Ochraceous-Salmon, Plate 15, lightly overcast with Carrot Red, Plate 14 in the center of the petals. Reverse of petals—Light Pinkish Cinnamon, Plate 29, very lightly overcast with Light Vinaceous Cinnamon, Plate 29. General tonality from a distance—Ochraceous-Salmon, Plate 15, lightly overcast with Carrot Red, Plate 14.

*Discoloration.*—General tonality at end of first day—Ochraceous-Salmon, Plate 15, lightly overcast with Carrot Red, Plate 14. Second day—Ochraceous-Salmon, Plate 15, very lightly overcast with Carrot Red, Plate 14. Third day—Ochraceous-Salmon, Plate 15.

Petals:

*Texture.*—Leathery; is not affected by wet or hot weather.

*Appearance.*—Inside—satiny. Outside—shiny.

*Form.*—Oval; notched.

*Arrangement.* — Imbricated (regularly arranged shingle-like).

*Petaloids in center.*—Few; large.

*Persistence.*—Drop off cleanly.

*Fragrance.*—Strong. Nature—fruity (russet apple).

*Lasting quality.*—On the plant—long. As cut flower—long.

*Genital Organs*

Stamens, anthers: Medium size; many; regularly arranged around styles. Color—Deep Chrome, Plate 3.

Stamens, filaments (threads): Medium length. Color—Rose Doree, Plate 1.

Pollen: Color—Pale Orange-Yellow, Plate 3.

Styles: Bunched; uneven length; medium length; thin.

Stigmas: Color—Empire Yellow, Plate 4.

Ovaries: All enclosed in calyx.

Hips: None.

Seeds: None.

*Plant*

Form: Bush.

Growth: Vigorous; upright.

Foliage: Compound of 5–7 leaflets.

*Size.*—Medium.

*Quantity.*—Normal.

*Color.*—New foliage; upper side—Spinach Green, Plate 5, lightly overcast with Garnet Brown, Plate 1; under side—Van Dyke Red, Plate 13. Old foliage: upper side—Varley's Green, Plate 18; under side—Light Elm Green, Plate 17.

*Shape.*—Oval.

*Texture.*—Upper side—glossy. Under side—smooth.

*Ribs and veins.*—Ordinary.

*Edge.*—Serrated (saw-toothed).

*Serration.*—Both double and single; small.

*Leaf stem.*—Color—Light Bice Green, Plate 17. Under side—prickly.

*Stipules.*—Medium length; bearded.

Wood:

*New wood.*—Color—Rinnemann's Green, Plate 18. Bark—smooth.

*Old wood.*—Color—Cress Green, Plate 31. Bark—smooth.

Thorns:

*Thorns.*—Quantity: on main stalks from base—ordinary; on laterals from stalk—ordinary. Form —narrow base; medium length; straight. Color (when young)—Acajou Red, Plate 13. Position—irregular.

*Prickles.*—Quantity: on main stalks—none. On laterals—none.

*Short needles.*—Quantity: on main stalks—none. On laterals—none.

I claim:

A new and distinct variety of rose plant of the hybrid tea class, substantially as herein shown and described, characterized particularly as to novelty by the unique combination of flower stamens of Deep Chrome color, a distinctive, attractive and unusual general color tonality of the flowers corresponding to Ochraceous-Salmon, lightly overcast with Carrot Red, and a fruity flower fragrance.

No references cited.